United States Patent
Haas

(10) Patent No.: US 11,446,076 B2
(45) Date of Patent: Sep. 20, 2022

(54) SINGLE-USE, LOW COST EXOTHERMIC SYSTEM FOR THERMOCOAGULATION OF TISSUE

(71) Applicant: Michael J Haas, Covington, LA (US)

(72) Inventor: Michael J Haas, Covington, LA (US)

(*) Notice: Subject to any disclaimer, the term of this patent is extended or adjusted under 35 U.S.C. 154(b) by 645 days.

(21) Appl. No.: 16/403,522

(22) Filed: May 4, 2019

(65) Prior Publication Data
US 2019/0343573 A1    Nov. 14, 2019

Related U.S. Application Data

(60) Provisional application No. 62/669,247, filed on May 9, 2018.

(51) Int. Cl.
*A61B 18/06* (2006.01)
*A61B 18/00* (2006.01)

(52) U.S. Cl.
CPC ...... *A61B 18/06* (2013.01); *A61B 2018/0091* (2013.01); *A61B 2018/00559* (2013.01); *A61B 2018/00589* (2013.01); *A61B 2018/068* (2013.01)

(58) Field of Classification Search
CPC .......... A61B 18/06; A61B 2018/00559; A61B 2018/00589; A61B 2018/0091; A61B 2018/068; A61F 2007/0036; A61F 7/034
See application file for complete search history.

(56) References Cited

U.S. PATENT DOCUMENTS

| | | | |
|---|---|---|---|
| 4,282,005 A * | 8/1981 | Sato | A61F 7/034 126/263.02 |
| 4,366,804 A | 1/1983 | Abe | |
| 5,117,809 A | 6/1992 | Scarings et al. | |
| 5,605,144 A | 2/1997 | Simmons et al. | |
| 6,629,417 B2 | 10/2003 | Haas et al. | |
| 6,824,555 B1 * | 11/2004 | Towler | A61B 18/06 607/113 |
| 6,832,995 B1 * | 12/2004 | Towler | A61B 18/06 606/27 |
| 7,652,228 B2 * | 1/2010 | Igaki | A61F 7/034 424/443 |
| 8,690,866 B2 * | 4/2014 | Brannan | A61B 18/06 604/82 |
| 9,308,123 B2 | 4/2016 | Drnek et al. | |
| 9,402,678 B2 | 9/2016 | Slatkine | |

(Continued)

FOREIGN PATENT DOCUMENTS

DE      41 39 029 C2     6/1993
DE   20 215 104 506 U1   1/2017

*Primary Examiner* — Michael F Peffley
*Assistant Examiner* — Amanda L Zink
(74) *Attorney, Agent, or Firm* — Joseph T Regard, Ltd plc

(57) ABSTRACT

A low cost, single-use disposable system for the thermocoagulation of tissue. The preferred embodiment of the present invention comprises an exothermic device for the treatment of cervical tissue or the like to provide low cost but effective treatment of, for example, precancerous conditions such as HPV (Human Papilloma Virus). The system provides an extremely cost efficient, easily implemented, single use, hygienic, rugged device which can be used in diverse conditions, requiring no power to operate, little training, and no other equipment.

8 Claims, 3 Drawing Sheets

(56) References Cited

U.S. PATENT DOCUMENTS

| | | | |
|---|---|---|---|
| 2012/0046656 A1* | 2/2012 | Brannan | A61B 18/06 606/28 |
| 2012/0215212 A1* | 8/2012 | Selzer | A61B 18/04 606/27 |
| 2013/0053839 A1* | 2/2013 | Hotto | A61B 18/082 606/30 |
| 2014/0074063 A1* | 3/2014 | Cressman | A61B 18/06 604/506 |
| 2014/0276577 A1* | 9/2014 | Thralls | A61B 18/0218 604/83 |

* cited by examiner

SINGLE-USE, LOW COST EXOTHERMIC SYSTEM FOR THERMOCOAGULATION OF TISSUE

BENEFIT CLAIM

The present application claims the benefit of U.S. Provisional Patent Application Ser. No. 62/669,247 filed May 9, 2018 entitled "Single-Use, Low Cost Exothermic System for Thermocoagulation of Tissue, listing as inventor Michael J. Haas of Covington, La., USA.

GENERAL FIELD OF THE INVENTION

The present invention relates to devices and methods for the application of heat to tissue in medical treatment, and particularly to a low cost, single-use system for the thermocoagulation of tissue. The preferred embodiment of the present invention comprises an exothermic device for the treatment of cervical tissue or the like to provide low cost but effective treatment of, for example, precancerous conditions such as HPV (Human Papilloma Virus). The system provides an extremely cost efficient, easily implemented, single use, hygienic, rugged device which can be used in diverse conditions, requiring no power to operate, little training, and no other equipment.

GENERAL BACKGROUND

Cervical cancer is a major cause of mortality of otherwise healthy females in many countries around the world. While it is avoidable in many cases with adequate screening and treatment of precancerous conditions, the local communities in many poor and/or rural areas, particularly in the developing world, lacks the infrastructure to provide such services. Many areas lack even the most basic necessities such as electricity and reliable access to clean water.

In those developing countries around the world where resources for uterine cervical (cervical) tissue problems are scarce, cryosurgery (freezing) and thermo-coagulation (scalding of the tissue) are most commonly used. Cryosurgery can be difficult for low to middle income countries to disseminate throughout a region for various reasons (cost, resource availability, product fragility).

A modality using electrical heat energy has started to emerge since approximately 2014 for these same conditions due to recent technological developments. In use, the cervical tissues are heated to just below boiling, which destroys tissue and creates an inflammatory process allowing the body to treat precancerous conditions along with the most common cause of cervical cancer, HPV (Human Papilloma Virus). Said modality uses either battery power or line current electricity to heat a resistive element to scald the cervical tissue. This system ultimately relies on a method of charging a battery system or using line voltage directly. The systems can also have a costly up front expense, making availability at many locations in LMIC (low to middle income countries) difficult if not impossible.

GENERAL SUMMARY DISCUSSION OF THE INVENTION

The present invention provides a novel and innovative, single-use, disposable, individually wrapped, aseptic device which is self-heated (utilizing an exothermic reaction) to provide an effective, easily implemented device to provide heat to a treatment area. It is noted that the present system can be single-use and disposable, and the unit could (in whole or part) be fabricated from compostable or otherwise degradeable (i.e., oxy-degradeable, bio-degradeable, UV-degradeable, etc) materials.

The preferred embodiment of the present invention provides a canister or container containing exothermic reactants, and an application tip formed to engage the cervix of a patient for thermal treatment of same. A reusable (or disposable) handle is provided to position the application tip of the device for treatment.

While the exemplary embodiment of the present invention is indicated as single use, an alternative embodiment of the present invention comprises a canister which includes refillable compartments for the exothermic material for multiple use, if desired. Still another embodiment could include refillable exothermic material and catalyst fluid compartments.

The present system includes the method of utilizing an exothermic reaction to heat an application surface for thermal treatment of a tissue area. The application surface is geometrically configured to optimize contact with the treatment area.

The present system includes a unique apparatus in the form of a combination exothermic heater and heat transfer system to provide efficient transfer of heat from the device to a targeted tissue area.

The present system further includes a unique integrated canister which stores at least one of the exothermic chemicals separately until needed, and an easy, safe and effective means to initiate the reaction to provide heat to the application surface.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 5A is a side, partially cutaway, partially close-up view of an alternative embodiment of canister 1 including a second, membrane-walled compartment for containing the fluid catalyst or the like.

DETAILED DISCUSSION OF THE INVENTION

Figure 1:
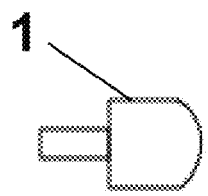
FIG. 1 is a side view of the canister 1 of the present invention.
Figure 2:
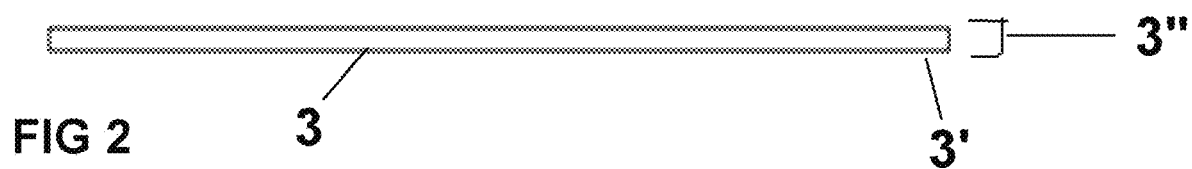
FIG. 2 is a side view of the handle 3 of the invention if FIG. 1.
Figure 3:
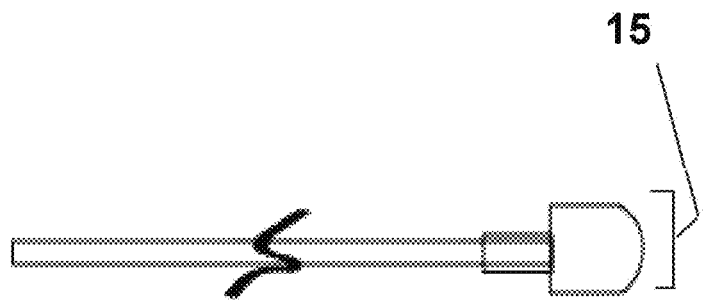
FIG. 3 is a side view of the handle 3 of FIG. 2 inserted into the canister 1 if FIG. 1.

Referring to the Figures, the preferred embodiment of the present device is particularly suitable for use in the field of Gynecology generally, and specifically to treatment of uterine cervical pre cancer and Cervical Intra epithelial Neoplasia (CIN 1,2,3) conditions.

The present device utilizes an exothermal chemical reaction to heat a cervical contact canister, which has a geometrically appropriate thermally conductive application tip raising it to treating temperature, which is formulated to reach and maintain this scalding temperature for the required treatment time.

Exothermic chemical combinations are well known and can be triggered by a variety of formulations utilizing effective and relatively low cost materials including (for example) Mg—Fe combinations triggered by saline mixtures.

These chemical combinations use processed chemicals in the 200-400-mesh particulate size range (for example), and are preferably pre-measured in volume and total energy delivered for different size cervical treatment tips, allowing the care giver to choose from various size and heat treatment formulations to provide the treatment as required for the particular patient. The combinations of types of exothermic chemicals, the mesh size, and the geometric chemical to application surface metal (aluminum, copper or stainless steel, aluminum being the most appropriate) configuration and the amount of catalyst material are just some of the variables that determine proper medical effective treatment.

Also, the size of the unit can vary depending on the size of the target area. For example, in use, the most common application tip size is 19 mm in diameter, but varies from 10 mm to 30 mm for larger or smaller cervix sizes. Pre-filled thermally conductive cervical tips can come with a pre-measured amount of chemical (for example, powdered iron or other materials as described herein) and activated by a separate saline (NaCL+H2O) or appropriate catalyst product, which may be separated within the canister or provided separately for use at the time of treatment, depending on the primary exothermic reaction chemical and circumstances of use, as described herein.

Continuing with FIGS. 1-4B, in the exemplary embodiment of the present invention, canister 1 contains an exothermic chemical 6 as shown is cylindrical with a rounded contact tip 15 forming a conical application surface 12 for contacting a patient's cervix, or other tissue or target area.

The curved contact tip of the exemplary embodiment of the present invention is made of aluminum (or other thermally conductive material), which forms the outer shell of the canister 1. The sidewalls of the cylindrical canister can have a thin outer insulating coating to prevent inadvertent heating of surrounding vaginal wall for safety and comfort.

The canister 1 has a front, first end 2 and rear, second end 2'. Associated with the rear, second end 2', is a receiver 4 formed to receive, via insertion 4', an end 3' or tip of holding rod 3 therein, so that the outer diameter (OD) 3" of holding rod 3 sliding engages the inner diameter 4" of receiver 4, so as to provide a handle for positioning and manipulation of the device in use.

Figure 4A:
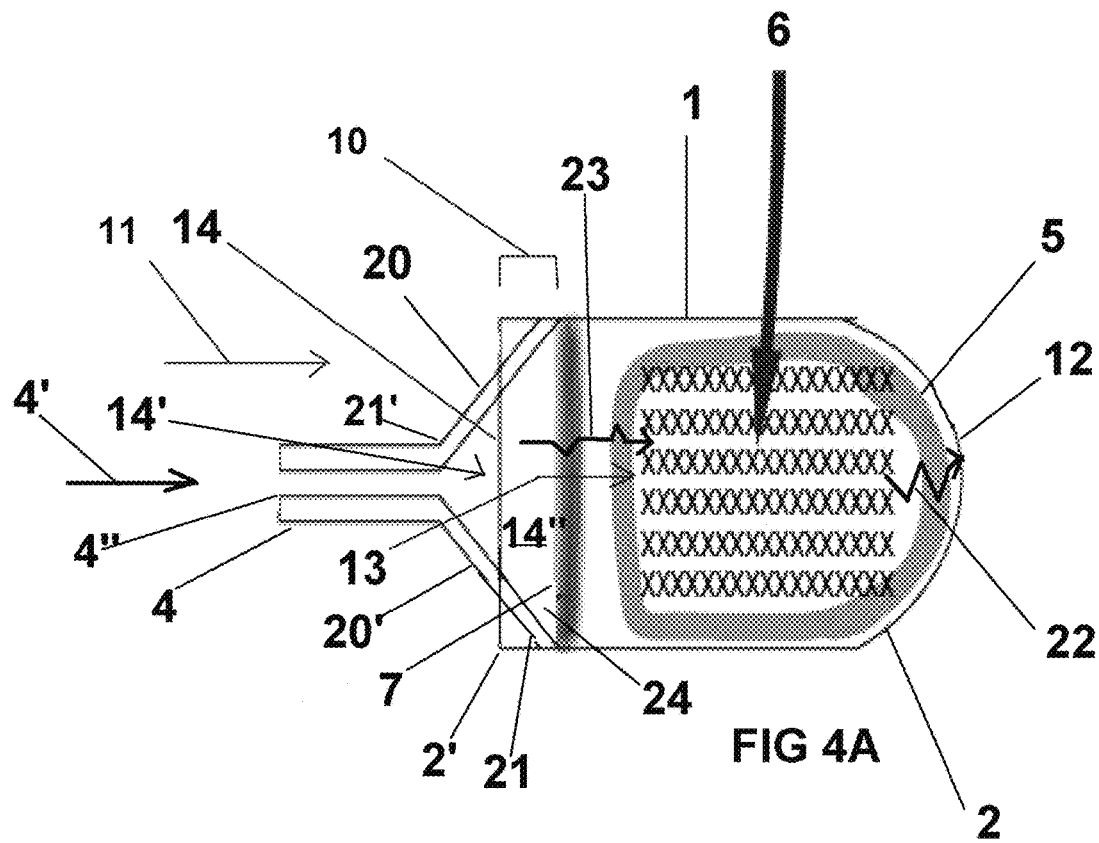
FIG. 4A is a side, partially cutaway, partially close-up view of the canister 1 of FIG. 1.
Figure 4B:
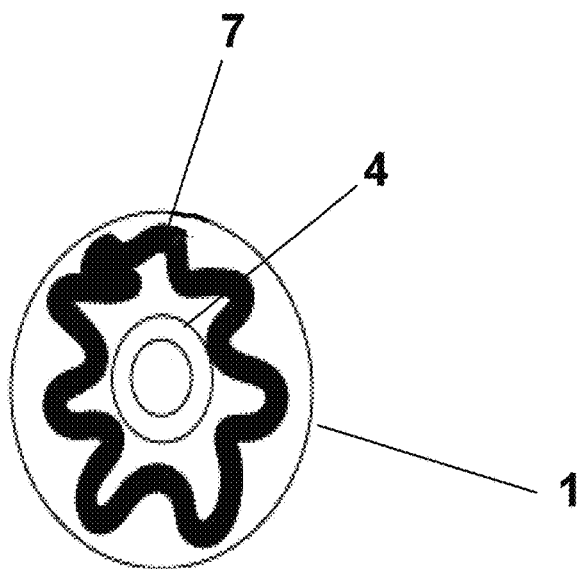
FIG. 4B is an end, partially cutaway view of the canister 1 of FIG. 4A.

As shown in FIGS. 4A-4B, the exemplary embodiment of the present invention utilizes three support members 20, 20' of metal or plastic emanating or otherwise associated with the rear, second end 2' of canister 1 (shown engaging the ID 14" formed by the opening within circular edge 14 of canister). Each support member 20, 20' has first 21 and second ends 21' which engage canister and support receiver 4, respectively, joining same.

As discussed, receiver 4 is formed to allow the insertion 4' of an end holding rod 3 therein, so as to attach the holding rod 3 to the to receiver to support canister 1, the holding rod 3 thereby forming a handle or extension for support and positioning of canister 1 and application or contact tip 15, as will be discussed in detail herein.

The second, rear end 2' of canister in the present illustrated exemplary embodiment has formed therein an ID 14" forming an opening 14' to receive a reactive fluid or catalyst (such as saline), which can be provided by the user at the time of treatment to trigger the exothermic reaction or contained until time of use, as will be further discussed herein.

Exothermic material 6 is contained by canister 1 as shown in FIG. 4A, the exothermic material is shown contained in a porous or mesh bag 5, pouch or other container so as to receive the saline (or other fluid reactant) therethrough.

The porous or mesh bag or pouch (formed of fabric, porous film or other fluid permeable material) is formed to contain the exothermic material 6 (particulate, powder or the like), and allow the liquid catalyst or reactive fluid (such as saline) to enter into 11 the canister (for example, via open 14' rear end), infuse into and through bag 5, and permeate 23 same to facilitate the engage the exothermic material 6 so as to facilitate an exothermic reaction, retaining the material and fluid during the exothermic reaction and allow transfer 22 of heat or thermal energy generated by said exothermic reaction to the contact or application 15 tip at the first end of canister 1, via the metal or other heat conducting material forming said canister 1, providing a heated contact or application 15 tip.

As shown, an exemplary exothermic material 6 can comprise, for example, a particulate magnesium—Iron alloy and its catalyst is a NaCl—H2O saline solution.

An open cell fluid permeable or porous membrane 7 to contain the mesh bag or pouch 5 is shown provided at the rear or second 2', open 14' end of canister 1, forming a retainer to retain the exothermic material within canister 1. The fluid permeable or porous membrane 7 facilitates the flow/transport of the catalyst (the reactant fluid) into the canister by allowing the fluid to permeate 23 or pass therethrough into the canister to the exothermic material.

The saline (or other) reactant solution or catalyst can be provided as a separate dropper bottle or the like with instructions as to how much volume of liquid (or drops) to drop or otherwise pass into 11 opening 14' at the rear or second end 2' of container or canister 1, where said reactant solution passes or permeates 23 through membrane 7 and mesh or porous bag 5 (if used) to react with exothermic chemical 6. Alternatively, a single use bottle or bag of the required volume of reactant fluid is provided which is likewise emptied into 11 the canister to provide the exothermic reaction and subsequent heating of the application surface 12 and contact tip 15.

In the preferred embodiment of the present invention, a space 10 is provided between the porous membrane 7 and edge 14 of the canister 1 (FIG. 4) which can provide a predesignated, optimal volume 24 to allow a user to dip the canister into a glass of reactant fluid (such as saline), and remove the canister from the fluid so that some of the fluid fills the volume between the membrane 7 and edge 14, then seeps 13 through to the exothermic chemical 6 in bag 5 so as to provide the optimal volume of reactant fluid for the exothermic chemical 6 in the canister for the desired reaction. Instead of dipping the canister into the fluid to fill the volume 24, alternatively the user can pour or otherwise fill the volume (such as by a flow of fluid into 11 volume 24 via opening 14') with the canister in a vertical position, until the liquid level fills the volume 24 (the liquid level reaches the edge 14' of canister), then allow the liquid to permeate 23 through membrane 7 into canister and exothermic material 6.

Figure 5A:
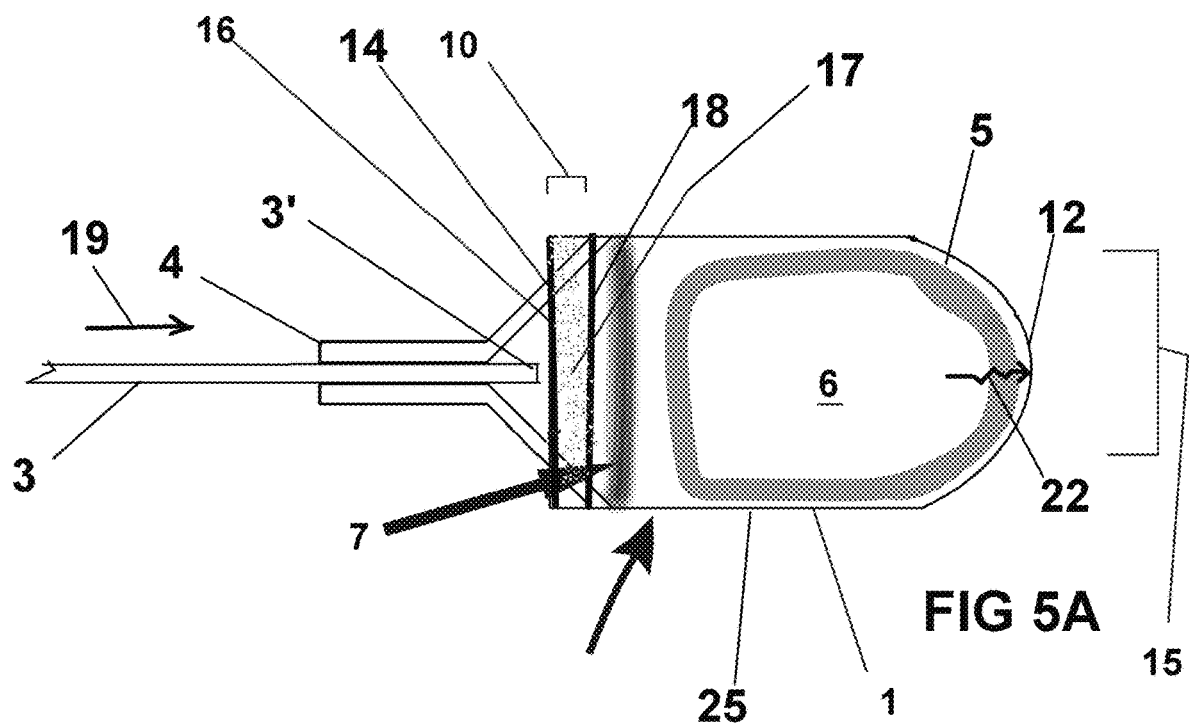
Figure 5B:
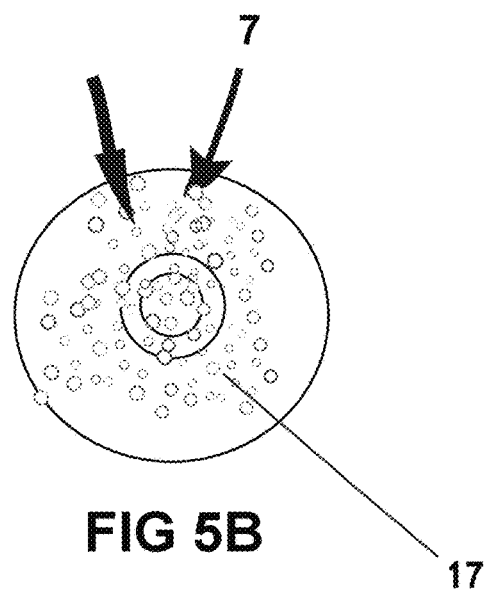
FIG. 5B is an end view of the invention of FIG. 5A, illustrating the exothermic reaction caused by the reaction fluid 17.

In another embodiment (FIGS. 5A and 5B) the exothermic material 6 and reactant fluid 17 or catalyst are provided and both stored in the canister 1 and separated by a containment membrane 18 or partition which can be ruptured at the time of use. A second membrane 16 situated near the edge 14 of canister encloses the catalyst or reactant fluid 17 within the container, between the first and second membranes 18, 16, respectively. In such an embodiment, a porous membrane 7 could be provided, but would not be required for most uses.

An embodiment of this type could incorporate the holding rod 3 forming the handle (FIG. 2) to provide the dual function of not only positioning the heated application tip at the target area of the patient but also form a triggering device for rupturing the membrane of partition, for example, by applying pushing 19 force to the holding rod (to use the end 3' of holding rod 3 to slide through receiver 4 to puncture or rupture frangible membrane 18 (which forms the partition separating the exothermic chemical and fluid reactant, for example), allowing reactant fluid 17 to spill or flow into the canister to engage the exothermic chemical 6.

Containment membrane 16 could be formed of a less frangible, more elastic material to allow the end 3' of holding rod 3 to push 19 against it, stretching it until it hits membrane 18 to rupture same, allowing the fluid reactant 17 to infuse through mesh or porous bag 5 (when used) to react with exothermic material 6 in the bag 5, generating heat which is transferred 22 through the canister 1 to application tip 15, while the more elastic containment membrane 16 remains intact.

Alternatively, as opposed to pushing force applied to the holding rod, another embodiment could be provided whereby one twisting the holding rod (for example facilitating further insertion 4' by holding rod 3 end 3' into receiver 4 (such as via threaded engagement), so that the handle tip is urged forward to engage a the frangible first membrane (the rod end or tip can be shaped to optimizing piercing or other engagement shape), for example.

The present invention thereby provides a ready to use uterine cervix tissue treatment apparatus that effectively scalds affected tissue utilizing an exothermic chemical reaction contained within a thermally conductive canister having little needs in terms of storage requirements, a long shelf life, and aseptically packaged (for example, via film packaging, bag or pouch or the like) for single use at the appropriate temperature and time with little to no preparation.

In the preferred embodiment canister/container containing the exothermic material, comprises a disposable thin metal canister shell. This shell consists of a conductive material such as aluminum. It holds the exothermic chemical, has a high heat transfer to receive and transfer heat to the contact tip 15 forming the application surface 12, and has a rear opening to the exothermic material so that the catalyst can be introduced without the exothermic material leaking out before, during and after activation of the exothermic reaction.

Apparatus and exothermic material are in intimate contact in optimized geometric configuration to allow the exothermic reaction best delivery of exothermic heat delivered. This configuration shown is the simplest, but many geometric exothermic-tip contact iterations can be undertaken, given thermal efficiency, cost to produce and patient safety.

Again, the exemplary apparatus' exothermic reaction heating material is Magnesium-iron alloy, although calcium carbonate or other appropriate combination may be utilized. Each chemical material has its own specific weights; mesh size and catalyst material depending on the size of the tip chosen by the medical professional prior to use.

The application or contact tip size 15 has a plurality for different women's cervix size needs. These tip sizes can vary between 10 mm and 30 mm for practical human cervical sizes.

The holding rod 3 or handle for the exothermic apparatus preferably is long and thin to allow entry into the vaginal vault through a vaginal spectrum or the like, and not impede visualization of the cervix contact in use. The diameter of the holding rod 3 or handle should preferably be less than 12 mm in diameter and between 50 and 75 mm in length. This handle can be constructed out of material that can withstand temperatures of 150 degrees centigrade without distortion. Plastics or metal materials are appropriate.

The apparatus canister 1, which contains the exothermic material, is constructed out of thermally conductive material, such as aluminum or copper.

The canister 1 forming the exothermal apparatus of the present invention ideally has a quick connect—disconnect interface with the holding rod such as the slotted receiver 4 shown formed to receive the end 3' of the holding rod, as shown in the figures.

The canister containing the exothermic material preferably has a conical tip to form the application surface 12, so as to facilitate proper cervix interface contact (when the cervix is the target area). The outside of the canister, not including the conical tip (i.e., the side 25 or outer diameter (OD) along its length) can have an insulating material provided so as to protect the non-treatable vaginal tissue from the heat of the process.

Temperatures and time are guided by specific medical protocols. Typical temperatures vary from 80-120 degrees centigrade (the most common at 100) and times vary from 40 seconds to two minutes (most common 45 seconds).

Listing of Elements 1 canister
2 first, second ends
3,','' holding rod, end, OD
4,',' canister receiver, insertion, ID
5 mesh bag or pouch
6 exothermic chemical
7 porous membrane
10 space
11 into
12 application surface
13 seep
14,',' edge of canister, opening, ID
15 contact tip
16 second membrane
17 reactant fluid
18 frangible, first membrane
19 push
20,' support members
21,' first, second ends
22 heat transfer
23 fluid passes through membrane
24 designated volume
25 side The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I Claim:

1. The method of applying heat to a target area, comprising the steps of:
   a. providing a canister containing an exothermic chemical, said canister formed of a heat conductive material, said canister having an exterior with an application tip shaped to engage a cervix of a patient;
   b. providing an extension to facilitate placement of said application tip to provide heat to said cervix;
   c. utilizing a catalyst fluid to react with said exothermic chemical to heat said application tip;
   d. positioning said application tip to engage said cervix with said extension, heating said cervix.

2. The method of claim 1, wherein in step d said cervix is heated so as to thermocoagulate a cellular tissue associated with said cervix.

3. The method of applying heat to a target area, comprising the steps of:
   a. providing a canister having an exothermic chemical situated therein, said canister comprising a heat conductive material, said canister having associated therewith an application tip formed to thermally engage a cellular tissue of a patient, said canister having situated therein a membrane to contain said exothermic chemical, and to provide a volume for receiving a catalyst fluid for activation of said exothermic material;
   b. providing an extension to facilitate placement of said application tip so as to provide heat to said cellular tissue;
   c. providing said pre-measured amount of catalyst fluid to said canister comprising the sub-steps of:
      ci. filling said volume provided in said canister with said catalyst fluid, and
      cii. allowing said catalyst fluid to permeate said membrane to react with said exothermic material.
   d. utilizing said catalyst fluid to react with said exothermic chemical to heat said application tip of said canister, providing a heated application tip;
   e. positioning said heated application tip to engage said cellular tissue with said extension, so as to heat said cellular tissue.

4. The method of claim 3, wherein in step "e" said heated application tip heats said cellular tissue so as to thermocoagulate said cellular tissue.

5. The method of applying heat to a target area, comprising the steps of:
   a. providing a canister having an exothermic chemical situated therein, said canister having associated therewith an application tip formed to thermally engage a cellular tissue of a patient, said canister having situated therein a fluid impermeable membrane to separate said exothermic chemical from a pre-measured amount of catalyst fluid for activation of said exothermic material;
   b. providing an extension having a tip, said extension engaging said canister;
   c. utilizing said extension to position said application tip to engage said cellular tissue at said target area;
   d. urging said tip of said extension into said canister so as to rupture said membrane in said canister and facilitate the flow of said catalyst fluid to said exothermic material;
   e. utilizing said catalyst fluid to exothermically react with said exothermic chemical to heat said application tip so as to heat said cellular tissue at said target area.

6. The method of claim 5, wherein in step "b" said extension engages said canister via a receiver, and in step "d" said extension slides through said receiver to allow said tip of said extension to penetrate said membrane with the application of force thereto.

7. The method of claim 6 wherein in step "b" there is provided a second membrane formed said canister, and in step "c" said catalyst fluid is provided between said first and second membranes.

8. The method of claim 7, wherein in step "d" said second membrane flexes to allow said tip of said extension to penetrate said first membrane.

* * * * *